United States Patent
Zhong et al.

(10) Patent No.: US 10,181,395 B2
(45) Date of Patent: Jan. 15, 2019

(54) MASS CALIBRATION KIT AND CALIBRATION METHOD FOR LOW-MASS REGION OF HIGH-RESOLUTION MASS SPECTROMETER IN NEGATIVE ION MODE

(71) Applicant: CENTRAL CHINA NORMAL UNIVERSITY, Hubei (CN)

(72) Inventors: Hongying Zhong, Hubei (CN); Xuemei Tang, Hubei (CN); Lulu Huang, Hubei (CN); Wenyang Zhang, Hubei (CN)

(73) Assignee: CENTRAL CHINA NORMAL UNIVERSITY, Hubei (CN)

( * ) Notice: Subject to any disclaimer, the term of this patent is extended or adjusted under 35 U.S.C. 154(b) by 61 days.

(21) Appl. No.: 15/533,011

(22) PCT Filed: Jan. 15, 2016

(86) PCT No.: PCT/CN2016/071030
§ 371 (c)(1),
(2) Date: Jun. 3, 2017

(87) PCT Pub. No.: WO2016/116012
PCT Pub. Date: Jul. 28, 2016

(65) Prior Publication Data
US 2018/0261441 A1  Sep. 13, 2018

(30) Foreign Application Priority Data
Jan. 21, 2015 (CN) .......................... 2015 1 0030498

(51) Int. Cl.
*H01J 49/00* (2006.01)
*G01N 27/64* (2006.01)

(52) U.S. Cl.
CPC .......... *H01J 49/0009* (2013.01); *G01N 27/64* (2013.01); *H01J 49/0027* (2013.01)

(58) Field of Classification Search
USPC ....................................................... 250/282
See application file for complete search history.

(56) References Cited

U.S. PATENT DOCUMENTS 7,781,173 B2 * 8/2010 Amshey ............. G01N 33/6842
435/4
8,313,789 B2 * 11/2012 Hotchkiss .......... A61K 31/7016
426/2

(Continued)

FOREIGN PATENT DOCUMENTS

CN      100504378 C      6/2009
CN      102645481 A      8/2012

(Continued)

OTHER PUBLICATIONS

Zhang Sen etc. Matrixes for Small Molecule Analysis Based on MALDI-MS (Progress in Chemistry, 2014,26( 1) : p. 158~166) Jan. 31, 2014.

(Continued)

*Primary Examiner* — Phillip A Johnston
(74) *Attorney, Agent, or Firm* — JCIPRNET

(57) ABSTRACT

A mass calibration kit and a calibration method for a low-mass area of a high-resolution mass spectrometer in negative ion mode. The mass calibration kit comprises semiconductor nanometer material suspension, a free fatty acid standard solution and a MALDI sample target cleaning liquid. The mass calibration method comprises: adjusting a voltage difference between a sample target of the mass spectrometer and a slit to be 20 V; dripping the semiconductor nanometer material suspension on the surface of the sample target till a solvent is completely volatilized and dried; dripping the free fatty acid standard solution on the surface of a semiconductor nanometer material till the solvent is completely volatilized and dried; and putting the sample target in the mass spectrometer for mass calibration, (Continued)

wherein calibration coefficients obtained after the instrument calibration can be used for correcting a sample mass spectrometric detection result. The calibration kit can effectively correct a low-mass area of a MALDI mass spectrometer in negative ion mode; mass spectrum signals are free of background interference; accurate measurement of the mass of a small molecule compound can be realized; and a relative error is less than 6 ppm.

7 Claims, 1 Drawing Sheet

(56) References Cited

U.S. PATENT DOCUMENTS

| 9,771,430 B2 * | 9/2017 | Tabas | A61K 31/47 |
| 2013/0123131 A1 * | 5/2013 | Purvis | C12Q 1/025 |
| | | | 506/9 |

FOREIGN PATENT DOCUMENTS

| CN | 103227096 A | 7/2013 |
| CN | 103245717 A | 8/2013 |
| CN | 104597114 A | 5/2015 |
| WO | 2007017701 A | 2/2007 |

OTHER PUBLICATIONS

"International Search Report (Form PCT/ISA/210)", dated Apr. 11, 2016, with English translation thereof, pp. 1-6.

* cited by examiner

MASS CALIBRATION KIT AND CALIBRATION METHOD FOR LOW-MASS REGION OF HIGH-RESOLUTION MASS SPECTROMETER IN NEGATIVE ION MODE

CROSS-REFERENCE TO RELATED APPLICATION

This application is a 371 application of an International PCT application serial no. PCT/CN2016/071030, filed on Jan. 15, 2016, which claims the priority benefits of China Application No. 201510030498.0, filed on Jan. 21, 2015. The entirety of each of the above-mentioned patent applications is hereby incorporated by reference herein and made a part of this specification.

BACKGROUND OF THE INVENTION

1. Field of the Invention

The present invention relates to the field of mass spectrometric detection, in particular, to a mass calibration kit and a correction method for a low-mass area of a high-resolution mass spectrometer in a negative ion mode.

2. Description of Related Art

MALDI refers to a matrix-assisted laser desorption/ionization mass spectrometry. Mass spectrometers of such type are widely applied to accurate mass measurement on various sample molecules. In such technology, sample molecules usually need to be mixed with a type of organic small molecules. The organic small molecules of this type include functional groups capable of absorbing laser energy and transfer the energy to the sample molecules to vaporize and ionize them, which are finally detected by a detector.

In an existing MALDI mass spectrometry technology, a small-molecule organic acid is usually used as a matrix. Major disadvantages of such a method include: (1) a series of background peaks are usually generated in the low-mass area; (2) sizes of crystal particles are inconsistent; and (3) low-mass sample signals are suppressed. In addition, the matrix causes serious contamination to the ion source, which not only ruins a quantitative relationship between the absolute signal intensity of the mass spectrum and the sample quantity, but also affects the spatial resolution. Because of the foregoing reasons, the MALDI mass spectrometer cannot analyze low-mass molecules by using a common matrix, especially in a negative ion mode. Currently, there is no commercialized calibration kit. Therefore, such low-mass molecules cannot be analyzed by using MALDI.

SUMMARY OF THE INVENTION

For disadvantages in the prior art, the present invention is directed to providing a mass calibration kit and a calibration method for a low-mass area of a high-resolution mass spectrometer in a negative ion mode.

A mass calibration kit for a low-mass area of a high-resolution mass spectrometer in a negative ion mode includes: a semiconductor nanometer material suspension, a free fatty acid standard solution, and a MALDI sample target cleaning solution.

According to the foregoing solution, the semiconductor nanometer material is ZnO, $(Bi_2O_3)_{0.07}(CoO)_{0.03}(ZnO)_{0.9}$, BN, AlN, $TiO_2$, or $Ga_2O_3$.

According to the foregoing solution, a solvent of the semiconductor nanometer material suspension is isopropanol.

According to the foregoing solution, the free fatty acid standard solution includes nine types of free fatty acids in total, namely, a free fatty acid C6:0, a free fatty acid C8:0, a free fatty acid C10:0, a free fatty acid C12:0, a free fatty acid C14:0, a free fatty acid C16:0, a free fatty acid C18:0, a free fatty acid C20:0, and a free fatty acid C22:0, and the nine types of free fatty acids have a same amount of substance.

According to the foregoing solution, a solvent of the free fatty acid standard solution is normal hexane.

According to the foregoing solution, components of the MALDI sample target cleaning solution are acetone whose volume concentration is 50% and normal hexane whose volume concentration is 50%.

A calibration method for a low-mass area of a high-resolution mass spectrometer in a negative ion mode includes the following steps:

(1) cleaning a MALDI mass spectrometer sample target by using a MALDI sample target cleaning solution, adjusting a sample target voltage, a hexapole voltage, an ion extraction voltage, and a slit voltage in a mass spectrometer ion source, so that a voltage difference between the sample target and the slit is 20 volts;

(2) dripping 1 microliter of semiconductor nanometer material suspension onto a surface of the sample target, keeping the sample target at a room temperature, and after a solvent in the semiconductor nanometer material suspension is completely volatilized and dried, obtaining a sample target whose surface is covered by a semiconductor nanometer material; and (3) taking 1 microliter of free fatty acid standard solution to drip it onto a surface of the semiconductor nanometer material on the sample target of step (2), after a solvent in the free fatty acid standard solution is completely volatilized and dried, placing the sample target into a mass spectrometer, and performing mass calibration in a calibration mode of the mass spectrometer, wherein a calibration coefficient obtained after the mass spectrometer is calibrated is automatically used to calibrate a result of sample mass spectrometric detection;

The process of the sample mass spectrometric detection includes: taking 1 microliter of a sample solution to drip it onto the surface of the semiconductor nanometer material of the sample target, naturally drying it, and placing the sample target into the mass spectrometer to perform the sample mass spectrometric detection.

According to the foregoing solution, the mass calibration is real-time calibration or off-line calibration.

In the present invention, a semiconductor nanometer material is selected based on the following principle: a bandgap of the semiconductor nanometer material is smaller than the laser photon energy of a MALDI mass spectrometer, and the electron mobility of the semiconductor material is high enough such that enough tunneling probability could be achieved in the applied electric field. The present invention is based on a laser activated electron tunneling as well as photoelectron capture ionization and dissociation. First, tunneling electrons are accelerated in an applied electric field, and then the tunneling electrons are captured by charge deficient atoms of adsorbed free fatty acids. The neutral fatty acid is switched to charged species with an unpaired electron. The molecular ion having an unpaired electron has extremely high reactivity, and further triggers the breaking of an α-position chemical bond. Kinetic energy of the electron is controlled under 20 eV, so that de Broglie wavelength of the electron is smaller than a length of a common chemical bond. In this case, the tunneling electrons can only be captured and would not cause reallocation of molecular vibrational energy, so that a mass-spectral peak generated by the breaking of a non-specific chemical bond is avoided. In the present invention, after the free fatty acid C6:0, the free fatty acid C8:0, the free fatty acid C10:0, the free fatty acid C12:0, the free fatty acid C14:0, the free fatty acid C16:0, the free fatty acid C18:0, the free fatty acid C20:0, and the free fatty acid C22:0 are vaporized and ionized, a series of low-mass mass-spectral peaks are obtained by using the MALDI mass spectrometer in a negative ion mode, masses of the mass-spectral peaks are uniformly different from each other by 28 Da, and accurate masses of all of the fatty acids are known. Therefore, the mass-spectral peaks may be used in mass calibration. In addition, the semiconductor nanometer material is not vaporized or ionized. Therefore, the semiconductor nanometer material does not generate background interference and does not contaminate the ion source.

The present invention has the following beneficial effects:

(1) As compared with an existing MALDI calibration kit, there are only high-mass calibration kits in a positive ion mode at present, and there is no commercialized kit that can be used for low-mass calibration in a negative ion mode. The present invention is based on a semiconductor nanometer material that is used for capturing laser activated tunneling electrons and ionizing different small-molecule free fatty acids. Because the semiconductor nanometer material does not generate background interference ions, and after the fatty acid is ionized, in a condition that a magnitude of an applied electric field is controlled, only one molecular ion whose accurate mass is known is generated, a low-mass calibration capability of MALDI in the negative ion mode is achieved, and limitation of a common MALDI matrix is overcome.

(2) The calibration kit of the present invention is environmental friendly, safe, and practical, can be easily prepared and preserved, and can effectively perform calibration for a low-mass area of a MALDI mass spectrometer in a negative ion mode. After mass calibration, accurate measurement can be performed on the mass of a small-molecule compound, and a relative error is less than 6 ppm.

(3) An operation process of the correction method of the present invention is simple and can be easily controlled. An obtained mass spectrum has a signal free of background interference, uniform mass distribution, high accuracy, high resolution, and a stable property.

DESCRIPTION OF THE EMBODIMENTS

In order to provide a better understanding of the present invention, the embodiments will be described in the following to further elaborate the content of the present invention, but the content of the present invention is not limited by the following embodiments.

Figure 1:
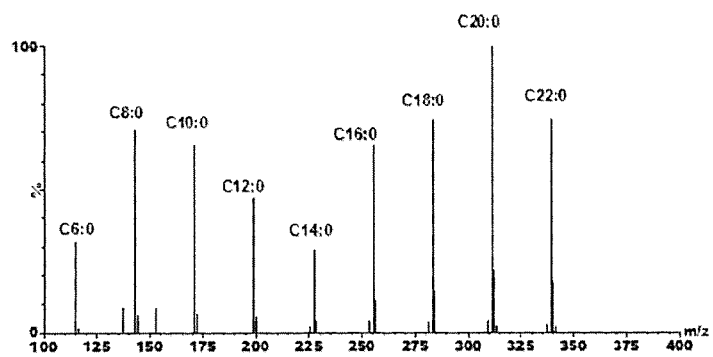
FIG. 1 is a diagram of mass-spectral peaks that are generated by nine types of free fatty acids C6:0, C8:0, C10:0, C12:0, C14:0, C16:0, C18:0, C20:0, and C22:0 which are uniformly different from each other by 28 Da.

In the following embodiments, a calibration method for a low-mass area of a high-resolution mass spectrometer in a negative ion mode is used and includes the following steps:

(1) cleaning a MALDI mass spectrometer sample target by using a MALDI sample target cleaning solution, adjusting a sample target voltage, a hexapole voltage, an ion extraction voltage, and a slit voltage in a mass spectrometer ion source, so that a voltage difference between the sample target and the slit is 20 volts;

(2) dripping 1 microliter of semiconductor nanometer material suspension onto a surface of the sample target, keeping the sample target at a room temperature, and after a solvent in the semiconductor nanometer material suspension is completely volatilized and dried, obtaining a sample target whose surface is covered by a semiconductor nanometer material;

(3) taking 1 microliter of free fatty acid standard solution to drip it onto a surface of the semiconductor nanometer material on the sample target of step (2), after a solvent in the free fatty acid standard solution is completely volatilized and dried, placing the sample target into a mass spectrometer, and performing mass calibration in a correction mode of the mass spectrometer, to obtain a diagram of mass-spectral peaks that are generated by nine types of free fatty acids C6:0, C8:0, C10:0, C12:0, C14:0, C16:0, C18:0, C20:0, and C22:0 which are uniformly different from each other by 28 Da, as shown in FIG. 1.

Preparation of the foregoing semiconductor nanometer material suspension includes: weighing 10 mg of semiconductor nanometer particles $(Bi_2O_3)_{0.07}(CoO)_{0.03}(ZnO)_{0.9}$, dissolving them in 1 mL of isopropanol, and performing ultrasonic oscillation for 1 minute to uniformly disperse the nanometer particles.

Preparation of the foregoing free fatty acid standard solution includes: taking a free fatty acid C6:0, a free fatty acid C8:0, a free fatty acid C10:0, a free fatty acid C12:0, a free fatty acid C14:0, a free fatty acid C16:0, a free fatty acid C18:0, a free fatty acid C20:0, and a free fatty acid C22:0 that have a same amount of substance, and using normal hexane as a solvent to obtain a free fatty acid standard solution whose solution concentration is 5 mg/mL.

Components of the foregoing MALDI sample target cleaning solution are acetone whose volume concentration is 50% and normal hexane whose volume concentration is 50%.

The foregoing mass calibration is real-time calibration or off-line correction.

Embodiment 1

Figure 2:
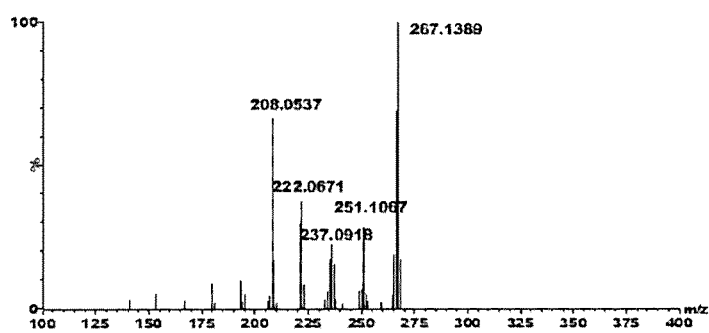
FIG. 2 is a diagram of a sample mass spectrum in Embodiment 1.

Mass spectrometric detection of oestrogen diethylstilbestrol includes the following specific operation steps:

(1) preparing a sample solution: weighing 100 mg of diethylstilbestrol and dissolving it in 1 mL of ethanol;

(2) transferring 1 microliter of the sample solution onto a surface of a semiconductor nanometer material that covers the foregoing sample target, and naturally drying it;

(3) adjusting a sample target, a hexapole, an extraction plate, and a slit voltage, so that a voltage difference between the sample target and the slit is 20 volts; placing the sample target into the mass spectrometer to perform mass-spectral detection, and after correcting a detection result by using a diagram of mass-spectral peaks of C6:0, C8:0, C10:0, C12: 0, C14:0, C16:0, C18:0, C20:0, and C22:0, a diagram of a sample mass spectrum is obtained, as shown in FIG. 2.

A combination of results of FIG. 1 and FIG. 2 indicates that: the mass spectrum has a signal free of background interference, uniform mass distribution, high accuracy, high resolution, and a stable property. After mass calibration, accurate measurement can be performed on measuring the mass of a small-molecule compound (such as oestrogen diethylstilbestrol), and a relative error between an actual detected value and a theoretical value is less than 6 ppm.

Embodiment 2

Figure 3:
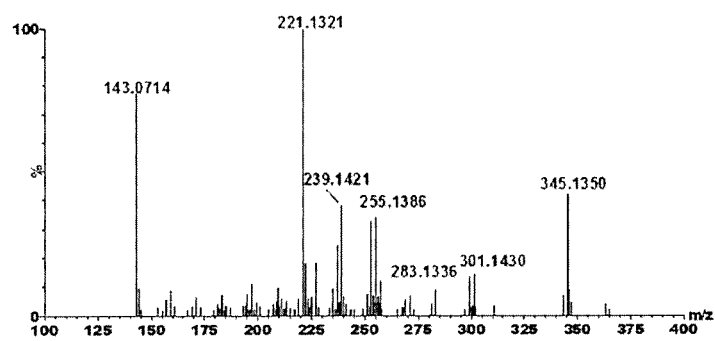
FIG. 3 is a diagram of a sample mass spectrum in Embodiment 2.

Mass spectrometric detection of phytohormone gibberellin includes the following specific operation steps:

(1) preparing a sample solution: weighing 100 mg of gibberellin and dissolving it in 1 mL of ethanol;

(2) transferring 1 microliter of the sample solution onto a surface of a semiconductor nanometer material that covers the foregoing sample target, and naturally drying it;

(3) adjusting a sample target, a hexapole, an extraction plate, and a slit voltage, so that a voltage difference between the sample target and the slit is 20 volts; placing the sample target into the mass spectrometer to perform mass-spectral detection, and after correcting a detection result by using a diagram of mass-spectral peaks of C6:0, C8:0, C10:0, C12:0, C14:0, C16:0, C18:0, C20:0, and C22:0, a diagram of a sample mass spectrum is obtained, as shown in FIG. 3.

A combination of results of FIG. 1 and FIG. 3 indicates that: the mass spectrum has a signal free of background interference, uniform mass distribution, high accuracy, high resolution, and a stable property. After mass calibration, accurate measurement can be performed on measuring the mass of a small-molecule compound (such as gibberellin), and a relative error between an actual detected value and a theoretical value is less than 6 ppm.

Apparently, the aforementioned embodiments are merely used as examples for describing the present invention more clearly, and are not used to limit the method for implementation. To those having ordinary skill in the art, various modifications and variations can be made based on the above description. All possible implementations could not and need not be exhaustively listed here. Therefore, all the obvious modifications and variations derived froze here still fall within the protective scope of the present invention.

What is claimed is:

1. A mass calibration kit for a low-mass area of a high-resolution mass spectrometer in a negative ion mode, comprising: a semiconductor nanometer material suspension, a free fatty acid standard solution, and a MALDI sample target cleaning solution, wherein, the semiconductor nanometer material is ZnO, $(Bi_2O_3)_{0.07}(CoO)_{0.03}(ZnO)_{0.9}$, BN, AlN, $TiO_2$, or $Ga_2O_3$.

2. The mass calibration kit according to claim 1, wherein a solvent of the semiconductor nanometer material suspension is isopropanol.

3. The mass calibration kit according to claim 1, wherein the free fatty acid standard solution comprises nine types of free fatty acids in total, namely, a free fatty acid C6:0, a free fatty acid C8:0, a free fatty acid C10:0, a free fatty acid C12:0, a free fatty acid C14:0, a free fatty acid C16:0, a free fatty acid C18:0, a free fatty acid C20:0, and a free fatty acid C22:0, and the nine types of free fatty acids have a same amount of substance.

4. The mass calibration kit according to claim 1, wherein a solvent of the free fatty acid standard solution is normal hexane.

5. The mass calibration kit according to claim 1, wherein components of the MALDI sample target cleaning solution are acetone whose volume concentration is 50% and normal hexane whose volume concentration is 50%.

6. A calibration method of the mass calibration kit for a low-mass area of a high-resolution mass spectrometer in a negative ion mode according to claim 1, comprising the following steps:

(1) cleaning a MALDI mass spectrometer sample target by using a MALDI sample target cleaning solution, adjusting a sample target voltage, a hexapole voltage, an ion extraction voltage, and a slit voltage in a mass spectrometer ion source, so that a voltage difference between the sample target and the slit is 20 volts;

(2) dripping 1 microliter of semiconductor nanometer material suspension onto a surface of e sample target, keeping the sample target at a room temperature, and after a solvent in the semiconductor nanometer material suspension is completely volatilized and dried, obtaining a sample target whose surface is covered by a semiconductor nanometer material;

(3) taking 1 microliter of free fatty acid standard solution to drip it onto a surface of the semiconductor nanometer material on the sample target of step (2), after a solvent in the free fatty acid standard solution is completely volatilized and dried, placing the sample target into a mass spectrometer, and performing mass calibration in a correction mode of the mass spectrometer, wherein a calibration coefficient obtained after the mass spectrometer is corrected may be automatically used to correct a result of sample mass spectrometric detection;

wherein the process of the sample mass spectrometric detection comprises: taking 1 microliter of a sample solution to drip it onto the surface of the semiconductor nanometer material of the sample target, naturally drying it, and placing the sample target into the mass spectrometer to perform the sample mass spectrometric detection.

7. The calibration method according to claim 6, wherein the mass calibration is real-time calibration or off-line calibration.

* * * * *